(12) United States Patent
Pacetti et al.

(10) Patent No.: US 9,474,834 B2
(45) Date of Patent: Oct. 25, 2016

(54) STENT WITH ALBUMIN COATING FOR ENHANCED THROMBORESISTANCE

(71) Applicant: Abbott Cardiovascular Systems Inc., Santa Clara, CA (US)

(72) Inventors: Stephen D. Pacetti, San Jose, CA (US); O. Mikael Trollsas, San Jose, CA (US); Alexander J. Sheehy, Redwood City, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 14/251,536

(22) Filed: Apr. 11, 2014

(65) Prior Publication Data
US 2015/0290363 A1 Oct. 15, 2015

(51) Int. Cl.
*A61L 31/10* (2006.01)
*A61L 33/16* (2006.01)
*A61L 31/08* (2006.01)
*A61L 31/16* (2006.01)
*A61L 33/12* (2006.01)

(52) U.S. Cl.
CPC ............ *A61L 31/10* (2013.01); *A61L 31/08* (2013.01); *A61L 31/16* (2013.01); *A61L 33/128* (2013.01); *A61L 2300/252* (2013.01); *A61L 2300/42* (2013.01); *A61L 2420/02* (2013.01)

(58) Field of Classification Search
CPC ....... A61L 31/10; A61L 33/12; A61L 33/16; A61L 27/227
USPC ............. 427/2.24, 2.25, 2.3, 2.28; 623/1.48
See application file for complete search history.

(56) References Cited

U.S. PATENT DOCUMENTS

| | | | | |
|---|---|---|---|---|
| 4,147,767 | A | * | 4/1979 | Yapel, Jr. ............... 424/499 |
| 5,073,171 | A | * | 12/1991 | Eaton .................... 604/266 |
| 5,447,724 | A | * | 9/1995 | Helmus ............ A61L 27/54 424/423 |
| 5,584,875 | A | * | 12/1996 | Duhamel ........... A61F 2/06 427/2.25 |
| 6,730,349 | B2 | * | 5/2004 | Schwarz ........... A61L 27/34 427/2.1 |
| 8,685,430 | B1 | | 4/2014 | Trollsas et al. |
| 2003/0050692 | A1 | * | 3/2003 | Sirhan ............... A61F 2/91 623/1.42 |
| 2004/0018228 | A1 | | 1/2004 | Fischell et al. |
| 2004/0180039 | A1 | | 9/2004 | Toner et al. |
| 2005/0032826 | A1 | | 2/2005 | Mollison et al. |
| 2005/0208093 | A1 | | 9/2005 | Glauser et al. |
| 2006/0008497 | A1 | | 1/2006 | Gabbay |
| 2007/0128246 | A1 | | 6/2007 | Hossainy et al. |

(Continued)

FOREIGN PATENT DOCUMENTS

| | | |
|---|---|---|
| EP | 0 246 809 | 11/1987 |
| WO | WO 91/17724 | 11/1991 |
| WO | WO 2004/021976 | 3/2004 |

OTHER PUBLICATIONS

An et al. Prevention of Bacterial Adherence to Implant Surfaces with a Crosslinked Albumin Coating In Vitro. Journal of Orthopaedic Research vol. 14, Issue 5, pp. 846-849, Sep. 1996.*

(Continued)

*Primary Examiner* — Cachet Sellman
(74) *Attorney, Agent, or Firm* — Squire Patton Boggs (US) LLP (57) ABSTRACT

Coatings for medical devices, the coatings including albumin, the methods of forming the coatings, and the coated medical devices are disclosed. In preferred embodiments the medical device is a bioabsorbable stent. The albumin coating layer improves the thromboresistance of the device.

20 Claims, 4 Drawing Sheets

(56) References Cited

U.S. PATENT DOCUMENTS

| | | | |
|---|---|---|---|
| 2009/0012604 A1 | 1/2009 | Schmitz et al. | |
| 2009/0061071 A1* | 3/2009 | McMorrow | A61L 31/14 |
| | | | 427/2.14 |
| 2009/0324682 A1 | 12/2009 | Popowski | |
| 2010/0087783 A1 | 4/2010 | Weber et al. | |
| 2012/0290075 A1 | 11/2012 | Mortisen et al. | |
| 2014/0186417 A1 | 7/2014 | Trollsas et al. | |
| 2014/0213765 A1* | 7/2014 | Lee | A61L 27/3616 |
| | | | 530/362 |

OTHER PUBLICATIONS

Albumin-blood (serum), MedlinePlus medical Encyclopedia 3 pgs. (2014).
Biomaterials Science, Ed. By Ratner et al., p. 240 (2004).
Dockal et al., "The three recombinant domains of human serum albumin", J. of Biol. Chem. vol. 274, No. 41, pp. 29303-29310 (1999).
Fasano et al., "The extraordinary ligand binding properties of human serum Albumin", IUBMB Life 57 (12), pp. 787-796 (2005).
Human Serum Albumin, molecular biology webpage, 6 pgs. Downloaded: http://bio.davidson.edu/courses/molbio/molstudents/spring2010/little/humanserumal., Mar. 11, 2014.
Human Serum Albumin, Wikipedia, the free encyclopedia, 8 pgs, downloaded: http://en.wikipedia.org/wiki/Human_serum_albumin, Mar. 11, 2014.
Kottke-Marchant et al., "Effect of albumin coating on the in vitro blood compatibility of Dacron® arterial prostheses", Biomaterials vol. 10, pp. 147-155 (1989).
Nonckreman et al., "Dual radiolabeling to study protein adsoption competition in relation with heocompatibility", J. of Biomed. Mat. Res. Part A, pp. 791-802 (2007).
Panchalingam et al., "Pulsed Plasma Discharge Polymer Coatings", ASAIO Journal, pp. M305-M309 (1993).
Quinlan et al., "Albumin: Biochemical Properties and Therapeutic Potential", Hepatology, pp. 1211-1219 (2005).
Schindel et al., "Comparision of Recombinant Human Albumin with Human Serum Albumin: Safety, Tolerability and Pharmacodynamics", J. Clinical Pharmacology 43 Abstract 76 (2003).
Sweryda-Krawiec et al., "A New Interpretation of Serum Albumin Surface Passivation", Langmuir vol. 20, No. 6, pp. 2053- 2056 (2004).
Takeda et al., "Conformational Change of Bovine Serum Albumin by Heat Treatment", J. of Protein Chem. vol. 8, No. 5 (1989).
"Application note: Viscosity measurement of a model protein solution of BSA", VROC™ A MEMS Device for small sample viscosity measurement, Rheosense Inc., 3 pgs, (2008).
International Search Report and Written Opinion for PCT/US2015/025146, mailed Jun. 30, 2015, 19 pgs.

* cited by examiner

STENT WITH ALBUMIN COATING FOR ENHANCED THROMBORESISTANCE

BACKGROUND OF THE INVENTION

1. Field of the Invention

This invention relates to coatings comprising albumin for medical devices, particularly stents, for treatment of coronary artery disease and peripheral artery disease.

2. Description of the State of the Art

This invention relates to the field of implantable medical devices (IMDs), more particularly to implantable medical devices having a coating comprising albumin, and optionally, also comprising drug(s) which can be released at a target site in a patient's body, and still more particularly to method of forming coatings on medical devices.

BACKGROUND

The discussion that follows is intended solely as background information to assist in the understanding of the invention herein; nothing in this section is intended to be, nor is it to be construed as, prior art to this invention.

Until the mid-1980s, the accepted treatment for atherosclerosis, i.e., narrowing of the coronary artery(ies) was coronary by-pass surgery. While effective, and having evolved to a relatively high degree of safety for such an invasive procedure, by-pass surgery still involves serious potential complications and, in the best of cases, an extended recovery period.

With the advent of percutaneous transluminal coronary angioplasty (PTCA) in 1977, the scene changed dramatically. Using catheter techniques originally developed for heart exploration, inflatable balloons were employed to re-open occluded regions in arteries. The procedure was relatively non-invasive, took a very short time compared to by-pass surgery and the recovery time was minimal. However, PTCA brought with it another problem, elastic recoil of the stretched arterial wall which could undo much of what was accomplished. In addition, PCTA failed to satisfactorily ameliorate another problem, restenosis, the re-clogging of the treated artery.

The next improvement, advanced in the mid-1980s, was use of a stent to scaffold the vessel walls open after PTCA. This for all intents and purposes put an end to elastic recoil, but did not entirely resolve the issue of restenosis. That is, prior to the introduction of stents, restenosis occurred in from 30-50% of patients undergoing PTCA. Stenting reduced this to about 15-30%, much improved, but still more than desirable.

In 2003, the drug-eluting stent (or DES) was introduced. The drugs initially employed with the DES were cytostatic compounds, compounds that curtailed the proliferation of cells that contributed to restenosis. As a result, restenosis was reduced to about 5-7%, a relatively acceptable figure. Today, the DES is the default medical standard for the treatment of coronary atherosclerosis, and is rapidly gaining favor for treatment of stenoses of blood vessels other than coronary arteries such as peripheral angioplasty of the superficial femoral artery.

With DES, two iatrogenic complications still remain. These two complications are restenosis and stent thrombosis. Restenosis, while in the single digit rate of occurrence is still troublesome for higher risk patient subsets such as diabetics, patients with long lesions, and patients with renal insufficiency. Thrombosis is a dreaded complication of stenting. High risk patient subsets for stent thrombosis include diabetics, patients with hyperlipidemia, smokers, patients with long lesions, and patients with overlapping stents. Further improvements in medical devices, such as stents, to reduce thrombosis may be advantageous.

INCORPORATION BY REFERENCE

All publications, patents, and patent applications mentioned in this specification are herein incorporated by reference to the same extent as if each individual publication or patent application was specifically and individually indicated to be incorporated by reference, and as if each said individual publication or patent application was fully set forth, including any figures, herein.

SUMMARY OF THE INVENTION

Embodiments of the present invention encompass methods of coating medical devices with albumin, and the coated devices.

Non-limiting embodiments of the invention are described the following labeled paragraphs:

[A] A method including:
providing a medical device having a surface;
disposing over the surface of the medical device a coating solution comprising albumin, a cross-linker, and a solvent;
removing the solvent to form a coating comprising albumin.

[B] In some embodiments, such as but not limited to the one described in paragraph [A], the cross-linker comprises at least one member of the group consisting of 1-(3-Dimethylaminopropyl)-3-ethylcarbodiimide HCl (EDC), glutaraldehyde, formaldehyde, ethylene glycol-bis-succinimide ester, disuccinimidyl tartrate, polyethylene glycol (PEG)-bis-maleimide, PEG-bis-succinimide ester, PEG-bis-acrylate, PEG-bis-vinylsulfone, and PEG-bis-thiol.

[C] In some embodiments, such as but not limited to those described in paragraphs [A] and [B], the method further comprises, after the removal of the solvent to form the coating comprising albumin, executing at least one additional processing operation.

[D] In some embodiments, such as but not limited to those described in paragraph [C], the or at least one additional processing operation is selected from sterilization and packaging.

[E] A method comprising:
providing a medical device having a surface;
disposing over the surface of the medical device a coating solution comprising albumin, and a solvent;
removing the solvent to form a coating comprising albumin; and
exposing the medical device to formaldehyde vapor to cross-link the albumin during the disposition of the coating solution over the surface of the device, during the removal of the solvent, after the removal of the solvent, both during the disposition of the coating solution over the surface of the device and during the removal of the solvent, both during the removal of the solvent and after the removal of the solvent, or during the disposition of the coating solution over the surface of the device, and during and after the removal of the solvent.

[F] In some embodiments, such as but not limited to the one described in paragraph [E], the duration of the exposure of the coated medical device to formaldehyde vapor is at least 5 minutes and not more than 24 hours.

[G] In some embodiments, such as but not limited to those described in paragraph [F], the duration of the exposure of the coated medical device to formaldehyde vapor is at least 5 minutes and not more than 360 minutes.

[H] In some embodiments, such as but not limited to those described in paragraphs [E]-[G], the vapor pressure of the formaldehyde is at least 0.1 Torr and not more than 760 Torr during the exposure.

[I] In some embodiments, such as but not limited to those described in paragraphs [A]-[H], the medical device provided comprises a coating comprising a drug on at least a portion of the medical device surface.

[J] In some embodiments, such as but not limited to those described in paragraph [I], the drug of the drug coating comprises at least one member of the group consisting of sirolimus, Biolimus, ridaforolimus, tacrolimus, temsirolimus, pimecrolimus, novolimus, myolimus, zotarolimus, everolimus, umirolimus, merilimus, 40-O-(3-hydroxypropyl)-rapamycin, 40-O-[2-(2-hydroxyl)ethoxy]ethyl-rapamycin, 40-O-tetrazolylrapamycin, and 40-epi-(N1-tetrazolyl)-rapamycin.

[K] In some embodiments, such as but not limited to those described in paragraphs [A]-[J], the solvent of the coating solution comprises water.

[L] A method comprising:
providing a medical device having a surface;
disposing over the surface of the medical device a coating solution comprising microparticulate albumin, and an organic solvent; and
removing the solvent to form a coating comprising albumin.

[M] In some embodiments, such as but not limited to the one described in paragraph [L], the coating solution further comprises a polymer and a drug.

[N] In some embodiments, such as but not limited to those described in paragraph [M], the polymer of the coating solution comprises at least one member of the group consisting of poly(D,L-lactide), block copolymers of poly(D,L lactide) and polyethylene glycol, poly(glycolide), block copolymers of poly(glycolide) and polyethylene glycol, poly(D,L-lactide-co-glycolide), block copolymers of poly(D,L-lactide-co-glycolide) and polyethylene glycol, poly(L-lactide), block copolymers of poly(L-lactide) and polyethylene glycol, poly(D,L-lactide-co-L-lactide), block copolymers of poly(D,L lactide-co-L-lactide) and polyethylene glycol, poly(D,L-lactide-co-D-lactide), block copolymers of poly(D,L lactide-co-D-lactide) and polyethylene glycol, poly(caprolactone-co-L-lactide), poly(caprolactone-co-D,L-lactide), poly(caprolactone-co-glycolide), poly(caprolactone-co-D-lactide), poly(caprolactone-block-L-lactide), poly(caprolactone-block-D,L-lactide), poly(caprolactone-block-glycolide), and poly(caprolactone-block-D-lactide).

[O] In some embodiments, such as but not limited to those described in paragraph [M], the polymer of the coating solution comprises at least one member of the group consisting of poly(hydroxyalkanoates), poly(hydroxyvalerate), poly(hydroxy-butyrate), poly(hydroxybutyrate-co-valerate), polyorthoesters, polyanhydrides, polyester amides, poly(amino acids), poly(glycolide-co-trimethylene carbonate), polymers and copolymers trimethylene carbonate, poly(caprolactone-co-trimethylene carbonate), and poly(lactide-co-trimethylene carbonate) where the lactide may be D-lactide, L-lactide, D,L-lactide, or meso-lactide.

[P] In some embodiments, such as but not limited to those described in paragraphs [M]-[O], the drug of the coating solution comprises at least one member of the group consisting of sirolimus, biolimus, ridaforolimus, tacrolimus, temsirolimus, pimecrolimus, novolimus, myolimus, zotarolimus, everolimus, umirolimus, merilimus, 40-O-(3-hydroxypropyl)rapamycin, 40-O-[2-(2-hydroxyl)ethoxy]ethyl-rapamycin, 40-O-tetrazolylrapamycin, and 40-epi-(N1-tetrazolyl)-rapamycin.

[Q] In some embodiments, such as but not limited to those described in paragraphs [L]-[P], the solvent of the coating solution comprises acetone.

[R] In some embodiments, such as but not limited to those described in paragraphs [L]-[Q], the micro-particulate albumin comprises particles consisting essentially of albumin.

[S] In some embodiments, such as but not limited to those described in paragraphs [L]-[Q], the micro-particulate albumin comprises particles comprising albumin grafted onto a polymer.

In some embodiments, such as but not limited to those described in paragraph [S], the polymer of the microparticulate albumin comprises at least one of the group consisting of poly(D,L-lactide), block copolymers of poly(D,L lactide) and polyethylene glycol, poly(glycolide), block copolymers of poly(glycolide) and polyethylene glycol, poly(D,L-lactide-co-glycolide), block copolymers of poly(D,L-lactide-co-glycolide) and polyethylene glycol, poly(L-lactide), block copolymers of poly(L-lactide) and polyethylene glycol, poly(D,L-lactide-co-L-lactide), block copolymers of poly(D,L lactide-co-L-lactide) and polyethylene glycol, poly(D,L-lactide-co-D-lactide), block copolymers of poly(D,L lactide-co-D-lactide), polyethylene glycol, poly(caprolactone-co-L-lactide), poly(caprolactone-co-D,L-lactide), poly(caprolactone-co-glycolide), poly(caprolactone-co-D-lactide), poly(caprolactone-block-L-lactide), poly(caprolactone-block-D,L-lactide), poly(caprolactone-block-glycolide), poly(caprolactone-block-D-lactide), polymers having functional groups of alcohols, such as without limitation, poly(ethylene-co-vinyl alcohol)), polymers having functional groups of thiols, such as without limitation polycysteine and polypropylene sulfide, polymers having functional groups of amines, such as without limitation, polylysine and polyallylamine, polymers having functional groups of aldehydes, such as without limitation polysaccharides, polymers having functional groups of vinyls, such as without limitation, polyacrylates and poly(meth)-acrylates with pendant vinyl groups, and polymers having functional groups of esters, such as without limitation, poly-alpha-hydroxyesters.

[U] In some embodiments, such as but not limited to those described in paragraphs [E]-[T], the method further comprises executing at least one additional processing operation.

[V] In some embodiments, such as but not limited to those described in paragraph [U], the or at least one additional processing operation is sterilization.

[W] In some embodiments, such as but not limited to those described in paragraphs [A]-[V], the albumin comprises human serum albumin.

[X] In some embodiments, such as but not limited to those described in paragraphs [A]-[V], the albumin comprises recombinant human serum albumin.

[Y] In some embodiments, such as but not limited to those described in paragraphs [A]-[V], the albumin comprises sub-domains of human serum albumin cleaved from the other sub-domains, sub-domains of recombinant human serum albumin cleaved from the other sub-domains, or a combination thereof.

[Z] In some embodiments, such as but not limited to those described in paragraphs [A]-[Y], the medical device is an intravascular medical device.

[AA] In some embodiments, such as but not limited to those described in paragraph [A]-[Z], the medical device is a stent or scaffold.

[AB] In some embodiments, such as but not limited to those described in paragraph [AA], the medical device is a bioabsorbable stent or scaffold.

DETAILED DESCRIPTION OF THE INVENTION

Use of the singular herein, expressly including the claims, includes the plural and vice versa unless expressly stated to be otherwise. That is, "a" and "the" refer to one or more of whatever the word modifies. For example, "a drug" may refer to one drug, two drugs, etc. Likewise, "the stent" may refer to one, two or more stents and "the polymer" may mean one polymer or a plurality of polymers. By the same token, words such as, without limitation, "stents" and "polymers" would refer to one stent or polymer as well as to a plurality of stents or polymers unless it is expressly stated or obvious from the context that such is not intended.

As used herein, unless specifically defined otherwise, any words of approximation such as without limitation, "about," "essentially," "substantially," and the like mean that the element so modified need not be exactly what is described but can vary from the description. The extent to which the description may vary will depend on how great a change can be instituted and have one of ordinary skill in the art recognize the modified version as still having the properties, characteristics and capabilities of the unmodified word or phrase. With the preceding discussion in mind, a numerical value herein that is modified by a word of approximation may vary from the stated value by ±15% in some embodiments, by ±10% in some embodiments, by ±5% in some embodiments, or in some embodiments, may be within the 95% confidence interval.

As used herein, any ranges presented are inclusive of the end-points. For example, "a temperature between 10° C. and 30° C." or "a temperature from 10° C. to 30° C." includes 10° C. and 30° C., as well as any temperature in between. In addition, throughout this disclosure, various aspects of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. As an example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Similarly, whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein, a "drug," refers to any substance that, when administered in a therapeutically effective amount to a patient suffering from a disease or condition, has a therapeutic beneficial effect on the health and well-being of the patient. A therapeutic beneficial effect on the health and well-being of a patient includes, but is not limited to: (1) curing the disease or condition; (2) slowing the progress of the disease or condition; (3) causing the disease or condition to retrogress; or, (4) alleviating one or more symptoms of the disease or condition.

As used herein, a drug also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease or condition in the first place; (2) maintaining a disease or condition at a retrogressed level once such level has been achieved by a therapeutically effective amount of a substance, which may be the same as or different from the substance used in a prophylactically effective amount; or, (3) preventing or delaying recurrence of the disease or condition after a course of treatment with a therapeutically effective amount of a substance, which may be the same as or different from the substance used in a prophylactically effective amount, has concluded.

As used herein, "drug," also refers to pharmaceutically acceptable, pharmacologically active derivatives of those drugs specifically mentioned herein, including, but not limited to, salts, esters, amides, and the like.

As used herein, a peptide sequence will refer to a molecule comprising from two to 50 amino acids. Chains of 50 amino acids or more are referred to herein as "proteins."

As used herein, a "polymer" refers to a molecule comprised of, actually or conceptually, repeating "constitutional units." The constitutional units derive from the reaction of monomers. As a non-limiting example, ethylene ($CH_2=CH_2$) is a monomer that can be polymerized to form polyethylene, $CH_3CH_2(CH_2CH2)_nCH_2CH_3$ (where n is an integer), wherein the constitutional unit is —$CH_2CH_2$—, ethylene having lost the double bond as the result of the polymerization reaction. The constitutional units themselves can be the product of the reactions of other compounds. A polymer may be derived from the polymerization of several different types of monomers or may be formed of several different types of constitutional units. Such polymers are referred to as "copolymers." Terpolymers are a sub-set of copolymers formed from three different types of constitutional units. Those skilled in the art, given a particular polymer, will readily recognize the constitutional units of that polymer and will equally readily recognize the structure of the monomer from which the constitutional units derive. As used herein, the term polymer refers to a molecule comprising more than 20 constitutional units.

Polymers may be straight or branched chain, star-like or dendritic, or one polymer may be attached (grafted) onto another. Polymers may have a random disposition of constitutional units along the chain, the constitutional units may be present as discrete blocks, or constitutional units may be so disposed as to form gradients of concentration along the polymer chain. In other words, the polymers used in this invention may be regular alternating polymers, random alternating polymers, regular block polymers, random block polymers or purely random polymers unless expressly noted otherwise. Polymers may be cross-linked to form a network.

As used herein, a molecule which has a chain length of 20 or fewer constitutional units is referred to as an "oligomer."

As used herein, a "crosslink" refers to a joining of two separate chains of a polymer by reaction of functional groups on the polymer with a multifunctional entity referred to as the cross-linking agent. As used herein, a "multifunctional crosslinking agent" is a compound having two or more functional groups that are capable of reacting with a functional group appended to the polymer backbone, or in some instances, to the terminal end of a polymer. As a non-limiting example, the functional group appended to the polymer backbone can be a hydroxyl, —OH, group and the multifunctional crosslinking agent can be a diisocyanate. The cross-linking reaction is shown schematically in Scheme 1:

Scheme 1 where the wavy line represents the polymer backbone and the crosslink comprises carbamate, —OC(O)NH—, groups. Of course, depending on how much diisocyanate is used, more than one hydroxyl group per polymer chain may become involved in crosslink formation. Typically, the cross-link joins non-terminal functional groups such that at the point where the cross-link joins the polymer, at least three chains emanate. It is also possible for the functional groups involved in a cross linking reaction to be disposed at the ends of the polymer chains, but if all the cross-linking agents are only bi-functional and all functional groups exist only a the end of the polymer chains, only chain extension would result. When the number of cross-linking groups is high enough such that multiple functional groups on a number of chains react with the cross-linking agent, including at least some non-terminal functional groups along the polymer chain backbone, the polymer forms a network.

As used herein, the terms "biodegradable," "bioabsorbable," "bioresorbable," and "bioerodable" are used interchangeably and refer to materials, such as but not limited to, polymers, that are capable of being completely degraded, eroded, and/or dissolved when exposed to bodily fluids such as blood and can be gradually resorbed, absorbed, and/or eliminated by the body. The processes of breaking down and absorption of the polymer can be caused by, for example, hydrolysis and metabolic processes. Conversely, the term "biostable" refers to materials that are not biodegradable.

As used herein, "solvent" is defined as a substance capable of dissolving one or more substances, capable of at least partially dissolving the substance(s), and/or dispersing one or more substances to form a uniformly dispersed solution at a selected temperature and pressure. A solvent can refer to one chemical compound, or a mixture of chemical compounds. A solvent can be a fluid. In some embodiments, dispersion occurs at the molecular- or ion-size level.

As used herein, "particle" may be a piece of matter held together by physical bonding of molecules, an agglomeration of particles held together by colloidal forces, and/or surface forces, or a piece of matter which is held together by chemical bonds, such as a cross-linked polymer network or one formed by ionic interactions, or a piece of matter held together by any combination of agglomeration, surface forces, colloidal forces, ionic interactions, Van der Waals forces, and chemical bonds. For the purposes of this disclosure, a particle will be defined as ranging in size from less than a one tenth of a nanometer to several millimeters in size. In addition, a particle may include one or more types of constituent molecules. Particle in this context does not refer to sub-atomic particles such as electrons, protons, neutrons, neutrinos etc.

The polydispersity of a group of particles represents the distribution of diameters within a particle group. Thus, the polydispersity can be represented by an average diameter and the standard deviation from the diameter. The average diameter can be a number average diameter, where the number average diameter=$\Sigma_i d_i n_i / \Sigma_i n_i$ where $n_i$ represents the number of particles with a diameter represented by $d_i$. Usually approximations are made and the distribution of particles by diameters is represented as a histogram, or in other words the particles are divided into smaller groups encompassing a smaller range of diameters and which is assigned a diameter near the center of that range. The surface area average diameter is determined by $(\Sigma_i f_i d_i^2)^{1/2}$, and the volume or mass average diameter is determined by $(\Sigma_i f_i d_i^3)^{1/3}$, where $f_i$ is $n_i/\Sigma_i n_i$. Thus, in the case of the surface area average, the weighting factor is the surface area represented by the class of particles of diameter $d_i$ while for the volume average diameter, the weighting factor is the volume represented by each class of particles of diameter $d_i$. Thus, since the surface area increases with diameter squared and the volume increases with diameter cubed, the surface area average diameter is greater than the number average diameter. The surface area diameter is in turn exceeded by the volume average diameter. The mass or weight average diameter is the same as the volume average diameter if the density of all of the particles is the same.

The standard deviation, which is a well-known statistical measurement, may be suitable to characterize the polydispersity, which is the range of particle diameters, for a narrow particle size distribution. Other measures of polydispersity include the d10 and d90 which refer to the diameters representing the threshold where 10% of the distribution falls below, and 90% of the distribution falls below, respectively. The average may be referred to as a d50. Thus for a number average, half or 50% of the number of particles have a diameter less than the d50. For an area average diameter, the d50 represents the point (diameter) where half the surface area represented by the group of particles is below the d50.

Another means for determining the average diameter is by the use of dynamic light scattering, which is also called photon correlation spectroscopy, and measures the diffusion of the particles in solution. The average diameter is the mean hydrodynamic diameter, and is close to the volume-average diameter. One method is outlined in the International Standards Organization ("ISO") 13321.

As used herein, a "nano-particles" refers to particles with a weight-average particle diameter, an average particle as determined from dynamic light scattering, or both, from 1 nm to 1000 nm, where nm is nanometer.

As used herein, a "micro-particles" refers to particles with a weight-average particle diameter, an average particle as determined from dynamic light scattering, or both, from 1 μm to about 1000 μm where 1 μm is micrometer.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, balloon-expandable stents, self-expandable stents, stent-grafts, grafts, artificial heart valves, foramen ovale closure devices, cerebrospinal fluid shunts, orthopedic fixation devices, and intrauterine devices.

Implantable medical devices can be made of virtually any material including metals and/or polymers. Devices may be made from bioabsorbable polymers, biostable polymers, or a combination thereof. The material from which the device is manufactured is not a limitation with respect to the present invention.

One type of implantable medical device is a stent or scaffold. Stents are implantable medical devices that are generally cylindrically shaped and function to hold open, and sometimes expand, a segment of a blood vessel or other vessel in a patient's body when the vessel is narrowed or closed due to diseases or disorders including, without limitation, tumors (in, for example, bile ducts, the esophagus, the trachea/bronchi, etc.), benign pancreatic disease, coronary artery disease, carotid artery disease and peripheral arterial disease. A stent can be used in, without limitation, the neuro, carotid, coronary, pulmonary, aorta, renal, biliary, iliac, femoral and popliteal, as well as other peripheral, vasculatures, and in other bodily lumens such as the urethra or bile duct. A stent can be used in the treatment or prevention of disorders such as, without limitation, atherosclerosis, vulnerable plaque, thrombosis, restenosis, hemorrhage, vascular dissection or perforation, vascular aneurysm, chronic total occlusion, claudication, anastomotic proliferation, bile duct obstruction and ureter obstruction.

Other medical devices may be referred to as insertable medical devices. That is any type of appliance that is totally or partly introduced, surgically or medically, into a patient's body or by medical intervention into a natural orifice, but the device does not remain in the patient's body after the procedure.

Another type of medical device is a vascular catheter, which is also an insertable medical device. A vascular catheter is a thin, flexible tube with a manipulating means at one end, referred to as the proximal end, which remains outside the patient's body, and an operative device at or near the other end, called the distal end, which is inserted into the patient's artery or vein. The catheter may be introduced into a patient's vasculature at a point remote from the target site, e.g., into the femoral artery of the leg where the target is in the vicinity of the heart. The catheter is steered, assisted by a guide wire than extends through a lumen, which is a passageway or cavity, in the flexible tube, to the target site whereupon the guide wire is withdrawn. After the guidewire is withdrawn, the lumen may be used for the introduction of fluids, often containing drugs, to the target site. For some vascular catheters there are multiple lumens allowing for the passage of fluids without removal of the guidewire. A catheter may also be used to deliver a stent or may be used to deliver a balloon used in angioplasty.

As used herein, a "balloon" refers to the well-known in the art device, usually associated with a vascular catheter, that comprises a relatively thin, flexible material, forming a tubular membrane, that when positioned at a particular location in a patient's vessel may be expanded or inflated to an outside diameter that is essentially the same as the inside or luminal diameter of the vessel in which it is placed. In angioplasty procedures, the balloon is expanded to a size larger than the luminal diameter of the vessel, as it is a diseased state, and closer to the luminal size of a healthy reference section of vessel. In addition to diameter, a balloon has other dimensions suitable for the vessel in which it is to be expanded. Balloons may be inflated, without limitation, using a liquid medium such as water, aqueous contrast solution, or normal saline solution, that is, saline that is essentially isotonic with blood.

A "balloon catheter" refers to medical device which is system of a catheter with a balloon at the end of the catheter.

A balloon, a catheter, and a stent differ. Stents are typically delivered to a treatment site by being compressed or crimped onto a catheter or onto a catheter balloon, and then delivered through narrow vessels to a treatment site where the stent is deployed. Deployment involves expanding the stent to a larger diameter, typically at least to the diameter of the vessel, once it is at the treatment site. Stents can be self-expanding or balloon expandable. The expanded stent is capable of supporting a bodily lumen for an extended period of time. In contrast, a balloon has a wall thickness that is so thin that the tubular membrane cannot support a load at a given diameter unless inflated with a fluid, such as a liquid or gas. Furthermore, a balloon is a transitory device that is inserted in the patient's body for only a limited time for the purpose of performing a specific procedure or function. Unlike a stent, dilatation balloons are not permanently implanted within the body.

The structure of stents is typically a generally cylindrical or tubular form, but the precise shape may vary from the shape of a perfect cylinder. Stents are generally cylindrical structures perforated with passages that are slots, ovoid, circular, the like shapes, or combinations thereof, where the perforations form at least 15%, preferably at least 25%, and even more preferably at least 35%, and often more, but not more than 99% of the exterior surface area of the cylinder. A stent may be composed of scaffolding that includes a pattern or network of interconnecting structural elements or struts. The scaffolding can be formed from tubes, or sheets of material, which may be perforated, rolled into a cylindrical shape and welded or otherwise joined together to form a tube. A pattern may be formed in the tube by laser cutting, chemical etching, etc. Stents may also be composed of helically wound or serpentine wire structures or other woven structures in which the spaces between the wires form the passages. A stent may be formed of corrugated rings, or may have a locking design.

Figure 1:
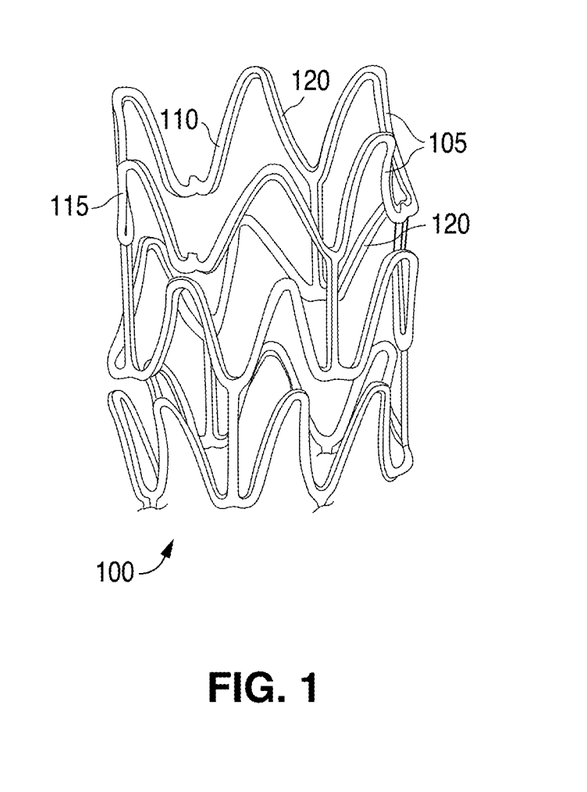
FIG. 1 depicts an exemplary stent scaffolding.

An example of a stent 100 is depicted in FIG. 1. As noted above, a stent may be a scaffolding having a pattern or network of interconnecting structural elements or struts 105, which are designed to contact the lumenal walls of a vessel and to maintain vascular patency, that is to support the bodily lumen. Struts 105 of stent 100 include luminal faces or surfaces 110, abluminal faces or surfaces 115, and sidewall faces or surfaces 120. The pattern of structural elements 105 can take on a variety of patterns, and the structural pattern of the device can be of virtually any design. Typical expanded diameters of a stent range from approximately 1.5 mm to 35 mm, preferably from approximately 2 mm to 10 mm, and for a coronary stent, from 1.5-6.0 mm. The length to diameter ratio of a stent is typically from 2 to 25.

In general, the body of a medical device is the device in the fully functional form before a coating or other material different from that of which the body is formed has been applied or attached. As an example, for a stent, the device body is the scaffolding. The embodiments disclosed herein are not limited to stents, or to the stent pattern, illustrated in FIG. 1.

Although the discussion that follows may make reference to a stent or stents as the medical device, the embodiments of the present invention are not so limited, and encompass any medical device which may benefit from the embodiments of the invention. Specifically, embodiments of the present invention encompass any blood-contacting medical device.

As noted above, the drug eluting stent (DES) is the default industry standard for the treatment of atherosclerosis, and is rapidly gaining favor for treatment of stenoses of blood vessels other than coronary arteries such as peripheral angioplasty of the superficial femoral artery. However, the use of drugs, such as anti-proliferative drugs, typically included in a coating often with a polymer over the stent surface, may interfere with vessel endothelialization. The antiproliferative drug release is necessary to avoid restenosis due to acute phase smooth muscle cell proliferation (SMP). Thus, antiproliferative drug release may be designed to rapidly decline to zero by 3 to 4 months after implantation so as not to interfere with endothelial cell growth and healing. In a human patient, endothelial cell layer growth can occur between post-stenting to 3 months, or up to six months, or more than six months after implantation.

Another issue with most coronary and other stents currently in use is that they are made of biostable or non-erodible materials, such as metals. Although there stents have been shown to be capable of preventing early and later recoil and restenosis, a stent made out of such biostable material retains its' mechanical or structural integrity and remains at the implant site indefinitely unless it is removed by intervention or is dislodged. Intervention to remove a stent presents risks to the patient and dislodgement can have significant adverse consequences on the patient. Leaving the stent at the implant site permanently also has disadvantages. Thus, an alternative is to use a stent, or device, made from a biodegradable material since the presence of the stent is necessary only for a limited period of time.

The development of a bioresorbable stent or scaffold obviates the permanent metal implant in vessel, allows for late expansive luminal and vessel remodeling, and leaves only healed native vessel tissue after the full absorption of the scaffold. Stents fabricated from biodegradable, bioabsorbable, and/or bioerodable materials such as bioabsorbable polymers can be designed to completely erode only after the clinical need for them has ended. Consequently, a fully bioabsorbable stent can reduce or eliminate the risk of potential long-term complications and of late thrombosis. However, it is believed that the bioabsorbable stent may still pose a risk of thrombosis during the limited period of time a bioabsorbable stent is present in a vessel.

After deployment, the stent maintains patency of the diseased section for a limited period of time until chemical degradation results in degradation of the radial strength to the point that the stent can no longer support the walls of the section of the vessel. The bioabsorbable stent provides patency to the stented segment for a finite period of time. Next, the radial strength of the stent decreases, making the stent unable to rigidly cage the vessel. The loss of radial strength is followed by a gradual decline of mechanical integrity, gradual loss of mass from the stent, and eventually disappearance of the stent from the stented segment. The time dependent radial strength profile of the stent includes an initial period after intervention in which the stent maintains its radial strength to prevent negative remodeling of the vessel which is then followed by a loss of radial strength.

Figure 2A:
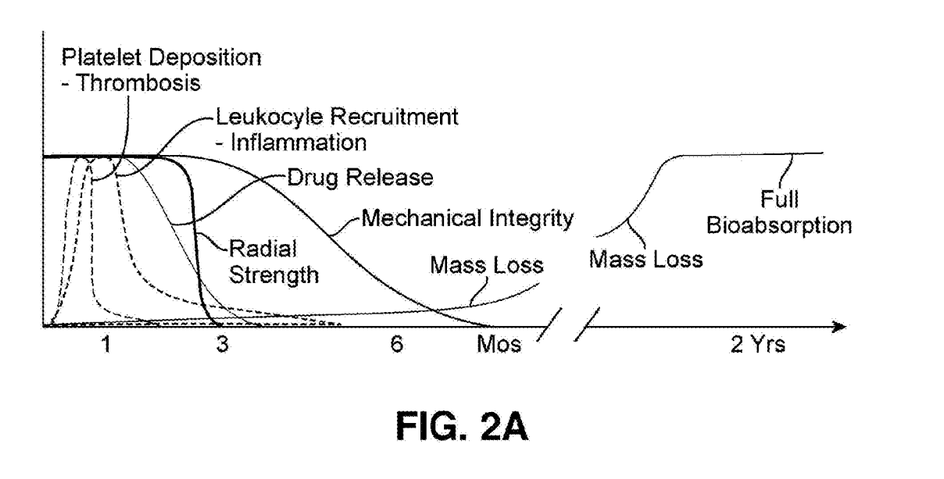
FIGS. 2A-C represent a schematic representation of an exemplary embodiment depicting the properties of an implanted bioabsorbable stent as a function of time.
Figure 2B:
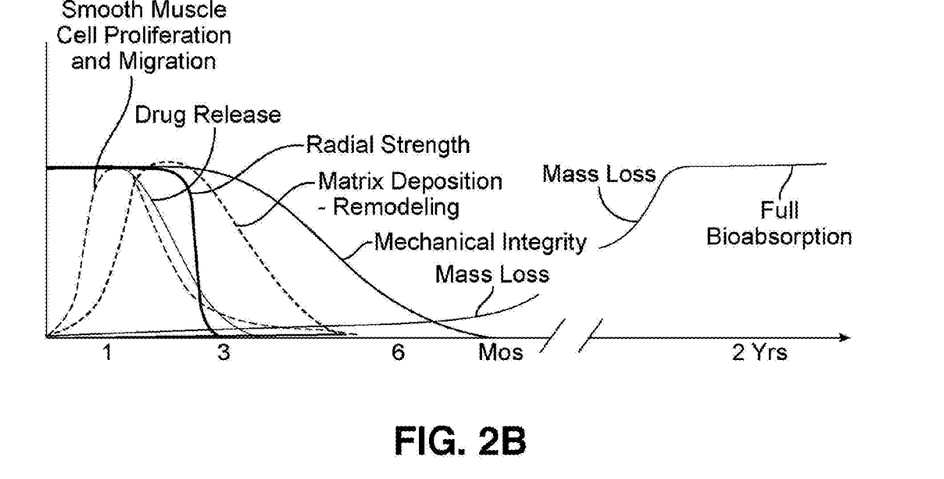
Figure 2C:
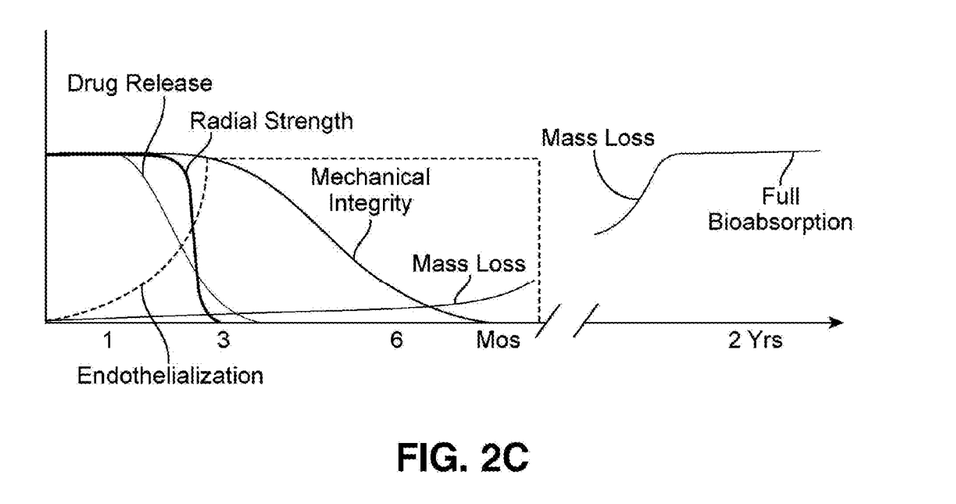

FIGS. 2A-C depict a schematic representation of exemplary time dependent behavior of a bioabsorbable stent, or scaffold, after intervention at an afflicted section of a vessel. In addition, FIGS. 2A-C also show expected biological responses of the vessel to the stent as a function of time.

Each of FIGS. 2A-C shows the time dependence of the stent properties, the radial strength, drug release, mechanical integrity, and erosion or mass loss. The radial strength of the stent is maintained for a period of time (in this case, after intervention) during which the stent supports the vessel walls. The stent then experiences a rapid deterioration in radial strength, due to molecular weight loss, and can no longer support the lumen walls (in this case, about 3 months after intervention). The drug release is maintained at a relatively constant level after intervention (in this case, between 1-1.5 months after intervention) followed by a relatively rapid decline to zero (in this case, between 3-4 months after intervention). The structural integrity is maintained at a relatively constant level for a period of time after intervention (in this case, about 3-4 months after intervention) followed by a gradual decline until a complete loss at a time greater than 6 months. The period of structural integrity retention is longer than radial strength retention as the rate of decline of mechanical integrity is more gradual.

There are several phases of biological response and vessel changes due to the intervention of the stent. The time period from intervention to about 1-3 months after intervention is referred to as the acute phase. FIG. 2A depicts two biological responses to the stent that occur during this phase, platelet deposition and leukocyte or white cell recruitment. Both processes are a normal part of vessel healing after scaffolding. However, excessive platelet deposition can be pro-thrombotic while chronic leucocyte recruitment will inhibit healing. These biological responses will dissipate more rapidly with the growth of neointima, and especially endothelium over the stent.

FIG. 2B depicts additional biological responses during the acute phase, smooth muscle cell proliferation (SMP) and matrix deposition. SMP occurs at the inner surface of the vessel wall in the stented section. The exemplary profile in FIG. 2B shows that the smooth muscle cell proliferation reaches a peak between one and two months and then decreases to negligible levels at about five months. Smooth muscle cell proliferation can be explained with reference to the structure of an arterial wall. Smooth muscle cell proliferation is expected to occur during a time period up to about three months after implantation of the stent. Smooth muscle cell proliferation should be controlled since it can lead to restenosis. Therefore, a bioabsorbable stent can release an antiproliferative agent, typically from a drug coating layer over the stent scaffolding, to control the smooth muscle cell proliferation. The drug release can occur up to two or four months after intervention.

Matrix deposition involves deposition of collagen and extra cellular matrix in the neointima layer combined with smooth muscle cells of a synthetic and proliferative phenotype. Matrix deposition is a key component of the remodeling process. Remodeling refers to a biological response that results in modification of the neointima layer formed from smooth muscle cell proliferation that facilitates a restoration of normal anatomy, and ultimately, normal function of the vessel.

Endothelialization refers to the formation of a layer of endothelial cells over the neointima layer and stent struts. FIG. 2C, which depicts cumulative endothelialization as a function of time, shows that endothelialization starts shortly after implantation and reaches a maximum just before three months. Endothelialization results in formation of hemocompatible surface between the blood and the stent. Endothelialization plays a critical role in the healing process with a bioabsorbable stent. Both the degree of endothelialization and timing of the endothelialization with respect to the stent behaviors are crucial outputs. Endothelialization of the vessel wall and stent struts is essential to prevent thrombosis associated with blood contacting stent surfaces, incomplete strut apposition (persistent or late-acquired), and embolization of stent material when mechanical integrity of the stent diminishes.

The presence of a blood-contacting surface of a foreign body, regardless of the level of hemocompatibility of the material of the stent, even if of a bioabsorbable material, may present a risk of thrombosis. In general, an endothelial layer plays a crucial role in reducing or preventing vascular thrombosis and intimal thickening. Specifically, the endothelial layer reduces or prevents deposition of prothrombotic proteins on the vessel wall or stent struts. Such deposition can contribute to or increase risk of thrombosis. Therefore, early and complete endothelialization of the vessel wall and stent are essential. Complete endothelialization should occur as rapidly as possible, preferably between 1 and 6 months to reduce the risk of or avoid the thrombo-embolic events associated with incomplete strut apposition and dislodgement of material in the vessel.

Therefore, stent surfaces are in contact with blood during a period after implantation, but prior to complete endothelialization. The degree of contact is initially very high immediately after implantation and decreases with time as endothelialization occurs. During this period there may be an increased risk of thrombosis arising from the contact of the stent with blood. The risk is expected to be greatest from the time period following implantation out to 6 months. It would be desirable to reduce this risk of thrombosis prior to complete endothelialization while not interfering with either the control of SMP or endothelialization.

Embodiments of the present invention encompass coatings for medical devices that improve the hemocompatibility of device, the coated medical devices, and methods of applying the coatings. In some embodiments, the medical device is formed of a bioabsorbable material. In some preferred embodiments, the medical device is a bioabsorbable stent. In particular, these embodiments apply during the period prior to endothelialization when the stent may pose a risk of thrombosis due to stent-blood contact. The coatings act synergistically with antiproliferative drugs by providing hemocompatibility during and without interfering with antiproliferative drug release. The hemocompatibility provided by the coating may be provided during a limited period of time, for example, during the antiproliferative drug release.

The risk of thrombosis presented by a stent is typically treated systemically with anti-coagulant and anti-platelet drugs. A common combination is aspirin with a thienopyridine such as clopidogrel or prasugrel. This combination is often called dual anti-platelet therapy. Systemic administration can be accomplished orally or parenterally including intravascularly, rectally, intranasally, intrabronchially, or transdermally. An anticoagulant is a substance that prevents coagulation; that is, it stops blood from clotting. Anti-platelet therapy inhibits platelet activation and aggregation. However, these systemic therapies can have side-effects. The most common side effects associated with dual anti-platelet therapy are itching, rashes, easy bruising, increased bleeding from injuries, gastrointestinal bleeding, and purplish spots on the skin. Purplish skin spots are caused by small amounts of bleeding under the skin. Bruising tends to be more severe when taking anticoagulants, and bleeding from wounds can be difficult to stop. A contraindication for surgery is dual anti-platelet therapy.

The embodiments of present invention provide advantages over systemic dual anti-platelet therapy. The coatings and coated medical devices, such as a coated stent, may reduce or replace systemic anti-coagulant therapy. The coatings that provide hemocompatibility are localized to the implant and can be configured to act only during the limited time that they are needed, and thus do not have the side-effects of systemic therapy. In many cases, the medical devices have a primary function and, as a secondary function, may be coated with a coating of one of the embodiments of this invention. An implantable medical device specifically designed and intended solely for the localized delivery of a drug is also within the scope of this invention. The embodiments of the coating layers of the present invention do not provide a significant fraction (less than 15%, preferably less than 10%) of the mechanical support for the medical device.

The various embodiments of the present invention include coatings including albumin, methods of forming such coatings, and medical devices with a coating including albumin. It has been shown that thromboresistance increases if a surface is passivated with albumin. A preferred albumin is human serum albumin. Human serum albumin is a protein of 595 amino acids that is about 66 to 67 kilo Daltons in molecular weight. Human serum albumin (HSA) is produced by the liver and is the most prominent protein in the blood. HSA has three domains named I, II, and III, each of which are formed of two helical sub-domains, A and B. HSA has a number of binding sites and transports a number of compounds in the blood. More specifically, HSA contains 35 cysteine residues, most of which include domain-linking disulfide bridges, but one of which is a free cysteine derived active thiol group. In addition to the free reactive thiol group which binds metals, HSA has an N-terminus which also binds metals. HSA may be obtained by fractionation of human plasma obtained from donors. Recombinant HSA is also produced by a number of vendors including Delta Biotechnology, Nottingham UK; ProSpec, Rehovot, Israel; Cyagen, Santa Clara, Calif., United States; Nova Biologics, Oceanside, Calif.; and Novozymes Biopharma, Bagsvaerd, Denmark. Recombinant HSA has the advantage of not being human sourced and thus has no risk of containing infectious agents. As serum albumin is a highly conserved protein, other mammalian sources such as bovine or porcine serum albumin are conceivable. However, HSA is preferred as there is no chance of an immunological response.

As used herein, unless expressly stated otherwise, "human serum albumin," refers to human serum albumin obtained from fractionating human plasma, recombinant human serum albumin, the sub-domains of HSA (obtained by cleaving fractionated HSA or recombinant methods), any two adjacent sub-domains of HSA as bound in HSA, or any combination thereof, where the sub-domains refers to the domains of HSA or two adjacent domains of HSA cleaved from (no longer covalently bound to) the other subdomain(s) (or made recombinantly to correspond to such domains). In some embodiments, the human serum albumin used is HSA fractionated from human plasma. In some embodiments, the HSA used is recombinant HSA. In some embodiments, the HSA is one or more of the sub-domains, not covalently bound to the other domains, while in other embodiments, the HSA used is two of the adjacent subdomains cleaved from the third subdomain or the recombinant equivalent, or a combination of two adjacent sub-domains. In some embodiments, the HSA is any combination of the above.

As used herein, a material that is described as "disposed over" an indicated substrate refers to, e.g., a coating layer of the material deposited directly or indirectly over at least a portion of the surface of the substrate. Direct depositing means that the coating layer is applied directly to the surface of the substrate. Indirect depositing means that the coating layer is applied to an intervening layer that has been deposited directly or indirectly over the substrate. A coating layer is supported by a surface of the substrate, whether the coating layer is deposited directly, or indirectly, onto the surface of the substrate. The terms "layer" and "coating layer" will be used interchangeably herein. A "layer" or "coating layer" of a given material is a region of that material whose thickness is small compared to both its length and width (e.g., the length and width dimensions may both the at least 5, 10, 20, 50, 100 or more times the thickness dimension in some embodiments). As used herein a layer need not be planar. For example, a layer may take on the contours of an underlying substrate. Coating layers can be discontinuous. As used herein, the term "coating" refers to one or more layers deposited on a substrate. A coating layer may cover all of the substrate or a portion of the substrate, for example a portion of a medical device surface. In some embodiments, the layers differ in the type of materials, the proportions of materials, or both, in the material applied. In some embodiments, a layer may have a concentration gradient of the components. One of skill in the art will be able to differentiate different coating layers or regions from each other based on the disclosure herein.

"Above" a surface or layer is defined as further from the substrate than the surface or layer, or over a surface or layer, measured along an axis normal to the substrate, but not necessarily in contact with the surface or layer.

"Below" is defined as the opposite of "above."

"Cover" is defined as "above" and in contact with.

Coating layers may be applied by any number of methods including spraying, dipping, ink jet printing, roll coating, electrostatic coating, chemical vapor deposition, ion beam deposition, use of a controlled-volume ejector, extrusion, molding, lamination, direct fluid application, or any combination thereof. A coating layer can be formed from a single-pass application or multiple-pass application, where a "pass" can be any single process step or single application step, or combination of steps, used to apply a coating material. Many coating layers comprise multiple passes. As a non-limiting example, multiple passes of a sprayer over a substrate, such as a medical device surface, may be needed to form a layer of the desired thickness.

A number of coating application methods involve the use of a coating solution. As used herein, "coating solution" refers to a combination of a solvent and a coating material which may be dissolved, partially dissolved, dispersed, or a combination thereof in the solvent. Typically, a coating solution is disposed over a substrate and the solvent removed to form a coating layer or part of a coating layer. As used herein, "removing the solvent" refers to either allowing the solvent to evaporate, allowing it to sublimate, or by using heat, a flow of a fluid such as air, a vacuum, or the like, to accelerate evaporation and/or sublimation.

Embodiments of the present invention encompass a coating including albumin, and particularly, HSA, over at least a portion of the surface of the device, and methods of forming such coatings as well as the coated devices. Although the discussion of the embodiments that follows may refer to human serum albumin, or HSA, it is understood that embodiments of the invention are not so limited and that other types of albumin may be used. In some embodiments, the coating including albumin, particularly HSA, covers all or substantially the entire outer surface of the device. For insertable or implantable medical devices, the "outer surface" is meant any surface however spatially oriented that is in contact with bodily tissue or fluids. For woven devices, the surface area in contact with bodily tissue or fluids includes that area that may be exposed upon flexing or movement of the device such as wire or strands at cross-over junction which move upon flexing thus exposing part of the surface underneath the junction. In some embodiments, the coating including albumin is disposed over at least a portion of the surface of a coated device. As a non-limiting example, the abluminal or the luminal side of a stent may be selectively coated.

In some embodiments, a coating layer including albumin is at least 50 wt % (weight %) albumin, at least 75 wt %, at least 90 wt %, at least 98 wt %, or at least 99 wt % albumin, but not more than 100 wt % albumin.

In some embodiments, the albumin is 100% native meaning it's as formed tertiary structure is intact. In other embodiments, the albumin is partially denatured. In some embodiments, the albumin is at least 0.5% denatured, but not more than 20% denatured, while in other embodiments, the albumin is at least 1% denatured, but not more than 15% denatured. Degree of nativity or denaturation may be measured by thermal analysis in the aqueous state, by circular dichroism, or by x-ray methods. Such methods are known to those of skill in the art.

The coating including albumin may include other coating layers. The coating layer including albumin may be on top of or in addition to other coating layers in the coating. In some embodiments, more than one layer of the coating includes albumin. In some embodiments, the coating layer with albumin is formed over a drug reservoir layer, which is formed over an optional primer layer. As used herein, a "primer layer" refers to a coating layer including a material such as a polymer that exhibits good adhesion characteristics with regard to the material of which the substrate is manufactured and whatever material is to be coated on the substrate. Thus, a primer layer serves as an adhesive intermediary layer between a substrate and materials to be carried by the substrate and is, therefore, applied directly to the substrate. As used herein, "drug reservoir layer" refers to a layer that includes one or more drugs. The layer may comprise one or more drugs applied neat (at least 95% drug), applied with an excipient such as a binder, or in combination with another material typically a polymer. Thus, in some embodiments, the drug is a component of a polymer matrix forming the drug reservoir layer. A polymeric drug reservoir layer is designed such that, by one mechanism or another, e.g., without limitation, by elution or as the result of biodegradation of the polymer, the drug is released from the layer into the surrounding environment. As used herein, a layer including albumin, but with no drugs is not considered to be a "drug reservoir layer." Embodiments of the present invention include coatings, methods of coating devices, and coated devices in which at least one layer of the coating (which may be the only layer of the coating) includes albumin. Any other number of layers may be included in the coating, such as a primer layer, a reservoir layer, etc. In preferred embodiments, the outermost coating layer of the coating includes albumin.

Embodiments of the present invention encompass a total coating thickness from 30 angstroms to 20 microns, preferably 30 angstroms to 10 microns, and more preferably 150 angstroms to 5 microns. For an individual coating layer, the thickness may range from 30 angstroms to 20 microns, preferably 30 angstroms to 10 microns, and more preferably 150 angstroms to 5 microns. An angstrom is $10^{-10}$ meter and a micron is a micrometer (μm or $10^{-6}$ meter). The coating may be a single molecular layer of albumin, or composed of several layers of albumin. In solution, the albumin molecule has dimensions of 30×130 angstroms (Nelson L N, Cox M M, Lehninger Principles of Biochemistry $3^{rd}$ Ed, Worth Publishers, New York, 2000, p. 175). Consequently, a single mono-layer may range in thickness from 30 to 150 angstroms depending on the adsorbed orientation of the molecule. Such a monolayer has an amount of albumin ranging from 0.20 to 1.5 μg/cm². However, when albumin is coated, the coating can comprise many layers of albumin. In this case, the coating can range into the nanometer ($10^{-9}$ meter) (nm) and micron range of thickness. Useful excipients to combine with albumin include, without limitation, polyethylene glycol, polypropylene glycol, propylene glycol, polyvinyl pyrrolidone, trehalose, mannitol, fructose, fatty acids, fatty acid esters, and phospholipids. Non-limiting examples of fatty acids include acetic acid, propanoic acid, butyric acid, caprylic acid, caproic acid, capric acid, lauric acid, myristic acid, palmitic acid, stearic acid, arachidic acid, behenic acid, lignoceric acid, and cerotic acid. Non-limiting examples of esters of fatty acids include all hydrocarbon esters of 1 to 16 carbon atoms, whether linear, branched, cyclic or aromatic, of all of the above mentioned fatty acids. The above cited excipients may be used individually, or in combination, and expressly including in combination with those excipients recited herein.

As an example, a stent with a drug eluting coating of a hydrophobic drug such as everolimus in a polymer coating may be further coated with HSA by spraying a solution including HSA dissolved in or dispersed in water or phosphate buffered saline (PBS) (having a pH of about 7.4±0.2) over the surface with removal of the water. The albumin may be at a percentage of about 2% by weight in the aqueous solution. In general, the albumin may be present at a level of 0.01 wt % to 25 wt % in solution, preferably 1 to 20 wt %, and more preferably, 5 to 15 wt % in solution. Preferably the level of albumin is such that the viscosity still allows for spraying of the solution. Other solvents that may dissolve or disperse albumin may be used. Non-limiting examples include glyme (dimethoxyethane) and diglyme (1-methoxy-2-(2-methoxyethoxy)ethane). Suitable solvents are those solvents typically used to dissolve proteins, such as without limitation, collagen. Water or an aqueous based solvent (at least 50% by weight water) is preferred. Solvents may be used individually or in combination.

In some embodiments, optionally in combination with any of the other embodiments disclosed herein, the albumin coating is cross-linked. In some embodiments, the coating solution includes a cross-linker in addition to the HSA. The cross-linker may react with amino and/or thiol groups on albumin. A cross-linked albumin coating is expected to be more durable and will have a longer residence time on the surface of the device. Thus, cross-linking albumin is expected to stabilize the coating. In some embodiments, the cross-linker that is chosen does not react with a drug of the device, whether in the body of the device, in a coating on the device, or both. Examples of cross-linkers, which may be added to an albumin coating solution or an albumin coating, include without limitation, 1-(3-Dimethylaminopropyl)-3-ethylcarbodiimide HCl (EDC), glutaraldehyde, formaldehyde, ethylene glycol-bis-succinimide ester, disuccinimidyl tartrate, polyethylene glycol (PEG)-bis-maleimide, PEG-bis-succinimide ester, PEG-bis-acrylate, PEG-bis-vinylsulfone, and PEG-bis-thiol. The cross-linkers may be used individually or in combination. In some embodiments, the coating solution is free of or essentially free of (<25 ppm) formaldehyde. In some embodiments, non-chemical means of cross-linking are used. Non-limiting examples include dehydrothermal crosslinking which is accomplished by heating the coating in a vacuum oven. Ultraviolet crosslinking may be accomplished by exposing the coating to UV radiation for a sufficient time at a sufficient intensity.

The amount of cross-linker may range from about 0.1 weight percent (wt %) to about 10%, or about 0.1 wt % to 10 wt %, of the weight of albumin in the coating solution, preferably from 0.5 wt % to 5 wt % (weight of cross-linker to weight of albumin, expressed as a percentage). Coatings with cross linker may require additional processing such as exposure to heat such as without limitation oven baking to drive the reaction to completion. The coating itself may be heated to a temperature between 28° C. and 45° C.

In other embodiments, a coating including HSA may be disposed over the surface of the device and subsequently cross-linked. In some embodiments, the subsequent cross-linking may be accomplished by exposing the albumin coating to formaldehyde vapor for a sufficient time to cross-link the albumin. The exposure of the coating layer with albumin to formaldehyde is not an exposure that occurs during the application of the coating layer including albumin to the medical device surface, or during the application of another layer to the medical device surface. The vapor pressure of the formaldehyde may be 0.1 mmHg (or Torr) and not more than 760 Torr during the exposure. The duration of exposure may be from 5 minutes to 24 hours, and in some embodiments, from 5 minutes to 360 minutes.

In some embodiments, micronized albumin may be added to a coating solution including a biodegradable polymer and optionally a drug. The solvents for many coating solutions are organic, and albumin is water soluble. In some embodiments, to obtain a coating solution with a polymer, a drug, and albumin, "microparticulate albumin" may be dispersed or homogenized into the solution. As used herein, "microparticulate albumin" is micro-particles, nano-particles, or both, which include albumin. In some embodiments, the "microparticulate albumin" has a weight-average particle diameter, a particle diameter determined by dynamic light scattering, or both, in the range of 10 nm to 100 μm, or about 10 nm to about 1 μm. The term "microparticulate HSA" refers microparticulate albumin where the albumin is HSA as defined above.

In some embodiments, the microparticulate albumin is at least 50 wt % albumin, at least 75 wt % albumin, at least 90 wt % albumin, at least 98 wt % albumin, at least 99 wt % albumin, or at least 99.5 wt % albumin, and not more than 100% albumin.

In some embodiments, the microparticulate albumin is formed by lyophilizing a dilute aqueous solution (about 0.1 to 5.0 wt %). The result of the lyophilization is fluffy sponge like particles which can be homogenized in a coating solution including an organic solvent, such as, but not limited to, acetone. The coating solution is disposed over at least a portion of a surface of a medical device to form a coating layer including albumin. The coating layer may also include a biodegradable polymer and optionally, a drug.

In some embodiments, optionally in combination with any of the other embodiments described herein, the microparticulate albumin is formed by making a water in oil emulsion in which the aqueous (water) phase includes albumin, and lyophilizing the solution. As an example, an aqueous solution of albumin at 20 wt % is added to an organic solvent, such as and without limitation, cyclooctane, and vigorously stirred to form an emulsion. Appropriate organic solvents for this process must be water immiscible meaning they absorb less than 10 wt % water. Suitable solvents in addition to cyclooctane include, without limitation, chloroform, methylene chloride, ethyl acetate, cyclohexane, hexane, heptane, diethyl ether, cottonseed oil, soybean oil, and mineral oil. The emulsion may be frozen and lyophilized to form microparticulate albumin. In some embodiments, if the water in oil emulsion will be frozen and lyophilized, the organic solvent has a freezing point accessible by a lyophilizer, which is typically $\geq -60°$ C. These solvents may be used individually or in combination.

In still other embodiments, a water in oil emulsion is made by emulsifying an aqueous solution of albumin into an oil phase, such as without limitation, cottonseed oil, oil, mineral oil, or a blend thereof, and then the water is removed under reduced pressure (such as but not limited to 10 Torr). The albumin is left as particles which may be filtered or centrifuged from the oil, with residual oil being removed by extraction with an organic solvent, such as but not limited to, acetone. For albumin formed in a water in oil emulsion, a small amount (about 5 wt % of total albumin) may denature at the water-oil interface. This denatured albumin, if it exists, may stabilize the particles.

It is expected that the micro particles or nanoparticles of albumin may remain dispersed in a coating solution for a sufficient time to allow for spraying onto a substrate.

In still other embodiments, optionally in combination with any of the other embodiments disclosed herein, the albumin may be grafted onto a polymer, the polymer of a type that is used to form a medical device coating. Examples of polymers include, without limitation, poly(D,L-lactide), block copolymers of poly(D,L lactide) and polyethylene glycol, poly(glycolide), block copolymers of poly(glycolide) and polyethylene glycol, poly(D,L-lactide-co-glycolide), block copolymers of poly(D,L-lactide-co-glycolide) and polyethylene glycol, poly(L-lactide), block copolymers of poly(L-lactide) and polyethylene glycol, poly(D,L-lactide-co-L-lactide), block copolymers of poly(D,L lactide-co-L-lactide) and polyethylene glycol, poly(D,L-lactide-co-D-lactide), block copolymers of poly(D,L lactide-co-D-lactide), polyethylene glycol, poly(caprolactone-co-L-lactide), poly(caprolactone-co-D,L-lactide), poly(caprolactone-co-glycolide), poly(caprolactone-co-D-lactide), poly(caprolactone-block-L-lactide), poly(caprolactone-block-D,L-lactide), poly(caprolactone-block-glycolide), poly(caprolactone-block-D-lactide), as well as other polymers having functional groups of alcohols, thiols, amines, aldehydes, vinyls, and esters, etc. The grafted polymers may be used individually, or in combination, and may further be combined with other coating materials, optionally including a drug, in forming a coating layer.

After the medical device has been coated, the coating including albumin in at least one layer of the coating, the medical device may be packaged and sterilized. In some embodiments, the coated device is packaged and stored in a container. The container may be designed to inhibit, prevent, or significantly minimize exposure of the stent to environmental conditions such as moisture, light, oxygen, etc. The device may be packaged in the container before or after sterilization of the stent. A device, such as a stent, can be sterilized by radiation, such as electron beam (e-beam), gamma radiation, or by a suitable sterilization gas such as ethylene oxide. Other methods of sterilization include hydrogen peroxide gas, plasma sterilization, and autoclaving. Ethylene oxide and e-beam sterilization are preferred sterilization modalities. In another embodiment, sterilization is by exposure to formaldehyde vapor with the medical device already packaged in a gas permeable package that will maintain a sterile barrier. In other embodiments, aseptic processing may also be employed.

Embodiments of the present invention encompass medical devices, particularly stents, and more particularly, bioabsorbable stents, with a coating including albumin. The coating may be any of those described above. Embodiments of the present invention encompass medical devices having a coating formed by the application of one or more coating layers where at least one (which may be the only coating layer) includes albumin. The method of application may be any of those described above. In preferred embodiments, the medical device is a bioabsorbable stent. In more preferred embodiments, the medical device is a bioabsorbable stent with a drug eluting coating formed of a drug and a bioabsorbable polymer or material, which may be the same polymer or material that the device body is formed from or may be a different polymer or material. In an even more preferred embodiment, the drug is everolimus, sirolimus (rapamycin), biolimus, ridaforolimus, tacrolimus, temsirolimus, pimecrolimus, novolimus, myolimus, zotarolimus, umirolimus, merilimus, 40-O-(3-hydroxypropyl)rapamycin, 40-O-[2-(2-hydroxyl)ethoxy]ethyl-rapamycin, 40-O-tetrazolylrapamycin, 40-epi-(N1-tetrazolyl)-rapamycin, or any combination thereof, and the bioabsorbable polymer of the coating is formed from one or more monomers, at least one monomer being a member of the group of L-lactide, D,L-lactide, D-lactide, caprolactone, trimethylene carbonate, glycolide, and meso-lactide.

With respect to the disclosure herein, the polymers disclosed for use in the embodiments of the present invention may be used individually, or in combination with other polymers, and expressly including, but not limited to, the other polymers specifically disclosed herein. Likewise, with respect to the disclosure herein, the drugs disclosed for use in the embodiments of the present invention may be used individually, or in combination with other drugs, and expressly including, but not limited to, the other drugs specifically disclosed herein.

In general, a medical device body or a coating can be made of a bioresorbable aliphatic polyester. Although some specific examples may be provided, it is understood that any of the specific examples may be used individually or in a blend with other polymers disclosed herein as well as other polymers in general. Exemplary biodegradable polymers for use in forming a bioabsorbable device body, or as a component of a coating, include poly(L-lactide) (PLLA), poly (D-lactide) (PDLA), polymandelide (PM), polyglycolide (PGA), poly(L-lactide-co-D,L-lactide) (PLDLA), poly(D,L-lactide) (PDLLA), poly(caprolactone-co-L-lactide), poly(caprolactone-co-D,L-lactide), poly(caprolactone-co-glycolide), poly(D,L-lactide-co-glycolide) (PLGA) and poly(L-lactide-co-glycolide) (PLLGA). With respect to PLLGA, the bioabsorbable device body or a coating can be made from PLLGA with a mole % of GA between 5-15 mol %, and more specifically, the PLLGA can have a mole % of (LA:GA) of 85:15 (or a range of 82:18 to 88:12), 95:5 (or a range of 93:7 to 97:3), or may be any commercially available PLLGA products identified as being 85:15 or 95:5 PLLGA. The examples provided above are not the only polymers that may be used in forming bioabsorbable device bodies or used in forming coatings. Many other examples can be provided, such as those found in Polymeric Biomaterials, second edition, edited by Severian Dumitriu; chapter 4.

Polymers that are more flexible or that have a lower modulus than those mentioned above may also be used in forming a bioabsorbable device body, or as a component of a coating. Other exemplary bioabsorbable polymers, with a lower modulus than those described above, include, without limitation, polycaprolactone (PCL), poly(trimethylene carbonate) (PTMC), polydioxanone (PDO), poly(4-hydroxy butyrate) (PHB), and poly(butylene succinate) (PBS), and blends and copolymers thereof.

In exemplary embodiments, higher modulus polymers such as PLLA or PLLGA may be blended with lower modulus polymers or copolymers with PLLA or PLGA to form a blend from which a device body is made, for use as a component of a coating, or both. Exemplary low modulus copolymers include poly(L-lactide)-block-polycaprolactone (PLLA-b-PCL) or poly(L-lactide)-co-polycaprolactone (PLLA-co-PCL). The composition of the blend may include 1-5 wt % of low modulus polymer.

Other polymers may be used as a component of a coating or in forming the device body. Non-limiting examples of these polymers include poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers include ethylene vinyl alcohol copolymer (commonly known by the generic name EVOH or by the trade name EVAL®), poly(butyl methacrylate), poly(vinylidene fluoride-co-hexafluoropropylene) (e.g., SOLEF® 21508, available from Solvay Solexis PVDF, Thorofare, N.J.), polyvinylidene fluoride (otherwise known as KYNAR®, available from Atofina Chemicals, Philadelphia, Pa.), ethylene-vinyl acetate copolymers, and polyethylene glycol.

The device body, a coating disposed over the surface of a device body, or both, may include a drug. Antiproliferative agents are a class of drugs that are particularly suitable. In general, the anti-proliferative can be a natural proteineous agent such as a cytotoxin or a synthetic molecule or other substances such as actinomycin D, or derivatives thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin I1, actinomycin X1, and actinomycin C1), all taxoids such as taxols, docetaxel, and paclitaxel, paclitaxel derivatives, macrolide antibiotics, rapamycin (sirolimus), everolimus, zotarolimus (ABT-578 manufactured by Abbott Laboratories, Abbott Park, Ill.), biolimus A9, ridaforolimus (formerly deforolimus, and also known as AP23573), tacrolimus, temsirolimus, pimecrolimus, novolimus, myolimus, 40-O-(3-hydroxyl)propyl-rapamycin, 40-O-[2-(2-hydroxyl)ethoxy]ethyl-rapamycin, 40-O-tetrazole-rapamycin, 40-epi-(N1-tetrazolyl)-rapamycin, FKBP-12 mediated mTOR inhibitors, perfenidone, prodrugs thereof, co-drugs thereof, and combinations thereof.

Another particularly suitable class of drugs is anti-inflammatory drugs. An anti-inflammatory drug can be a steroidal anti-inflammatory drug, a nonsteroidal anti-inflammatory drug, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lornoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, codrugs thereof, and combinations thereof.

The drugs used may have anti-proliferative and/or anti-inflammatory properties or may have other properties such as antineoplastic, antiplatelet, anti-coagulant, anti-fibrin, antithrombonic, antimitotic, antibiotic, antiallergic, antioxidant as well as cystostatic properties. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax® (bivalirudin, Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide, nitric oxide donors, super oxide dismutases, super oxide dismutase mimetics, 4-amino-2,2,6,6-tetramethylpiperidine-1-oxyl(4-amino-TEMPO), estradiol, anticancer agents, and dietary supplements such as various vitamins. Examples of such cytostatic substance include angiopeptin, angiotensin converting enzyme inhibitors such as captopril (e.g. Capoten® and Capozide® from Bristol-Myers Squibb Co., Stamford, Conn.), cilazapril, and lisinopril (e.g. Prinivil® and Prinzide® from Merck & Co., Inc., Whitehouse Station, N.J.). A non-limiting example of an antiallergic agent is permirolast potassium. Other therapeutic substances or agents which may be appropriate include alpha-interferon, and genetically engineered epithelial cells. The foregoing substances are listed by way of example and are not meant to be limiting. Other active agents which are currently available or that may be developed in the future are equally applicable. Some drugs listed above belong to more than one category.

EXAMPLES

The following examples are given to aid in understanding the invention, but it is to be understood that the invention is not limited to the particular materials or procedures of examples.

Example 1

The ability of albumin to passivate the surfaces of drug eluting stents (DES) was evaluated at Abbott Vascular via a porcine ex-vivo shunt. In this study, the test articles were:
XIENCE® V, 3.0×18 mm
ENDEAVOR RESOLUTE™, 3.0×18 mm
XIENCE® V, 14 day eluted in serum albumin
ENDEAVOR RESOLUTE™, 14 day eluted in serum albumin The XIENCE® V drug-eluting stent is a stent having a metal body of CoCr L-605 ASTM F90-09 and having a fluoropolymer coating including everolimus. The ENDEAVOR RESOLUTE™ is a stent formed of CoNi MP35N ASTM F562-07 with a biostable polymer coating that includes zotarolimus. The XIENCE® V 14 day eluted and ENDEAVOR RESOLUTE™ 14 day eluted are the above stents that have been placed in simulated in-vivo usage for 14 days which allows for the drug to release, and for the coatings to evolve. Drug release of the stents was performed with the stents deployed in silicone tubing of 3.0 mm ID (inner diameter) under sterile conditions. A solution of phosphate buffered saline (PBS) (pH 7.4±0.2) with 1% bovine serum albumin (BSA) at approximately 37° C. was pumped though at a flow rate of 43 ml/min and the solution changed every 3 days. The simulated in-vivo usage and drug release (drug elution) effectively coated the stents with albumin. For XIENCE® V approximately 60% of the XIENCE® V drug was released/eluted during the 14 day period.

Stents were evaluated in a porcine shunt model. The porcine shunt model is created by cannulating the femoral artery and vein and shunting blood through silicone tubing. Stents are deployed in short lengths of silicone tubing, weighing the combination, and then placing the combination in the shunt for 30 minutes. At the end of the 30 minutes, the combination of the deployed stent in the silicone tube was removed and was weighed again. Two controls were used: a silicone tube without any stent, and a VISION® bare metal stent deployed in the silicone tube. Six of each of the four types of test articles, and six of each of the two controls were evaluated.

Figure 3:
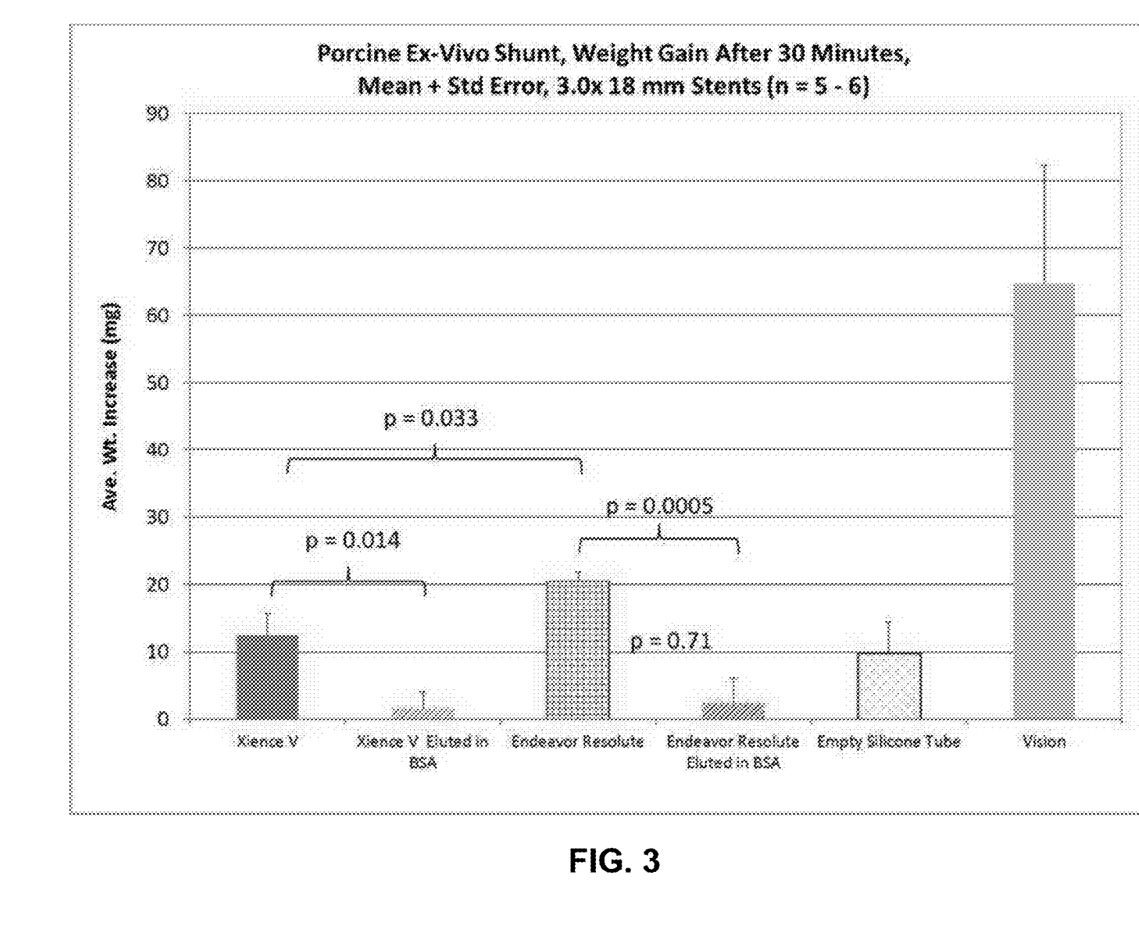
FIG. 3 depicts the results of thrombus accumulation in a porcine ex-vivo shunt model.

FIG. 3 shows the thrombus weight for the tested groups. As shown in FIG. 3, XIENCE® V is statistically more thromboresistant than VISION® in this model. As the stent is the same, the strut thickness is greater for XIENCE® V, which is due to a combination of the drug and the coating. The everolimus in the coating on the XIENCE® V has some antiplatelet effect. In addition, the fluoropolymer in the coating on the XIENCE® V is thromboresistant. XIENCE® V is statistically less thrombogenic than ENDEAVOR RESOLUTE™, and this is an effect of the entire stent system including strut thickness, stent pattern, drug and polymer coating. While the elution in BSA was performed to remove drug, it also had the effect of thoroughly coating the stents with albumin. For both XIENCE® V and ENDEAVOR RESOLUTE™, incubation in albumin lowered the thrombogenicity as compared to the same articles that were not subjected to the drug elution prior to deployment in the ex-vivo shunt model. In other words, albumin coated XIENCE® V and ENDEAVOR RESOLUTE™ are both statistically lower in thrombogenicity than their uncoated counterparts. Although XIENCE® V 14 day eluted, that are effectively albumin coated, is less thrombogenic than ENDEAVOR RESOLUTE™ 14 day eluted, the difference is not statistically significant.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method comprising:
disposing over a surface of a medical device a coating solution comprising a polymer, a drug, microparticulate albumin, and an organic solvent; and
removing the solvent to form a coating comprising albumin.

2. The method of claim 1, wherein the polymer of the coating solution comprises at least one member of the group consisting of poly(L-lactide), poly(D-lactide), poly(D,L-lactide), poly(L-lactide-co-glycolide), poly(D-lactide-co-glycolide), poly(caprolactone-co-L-lactide), poly(caprolactone-co-D,L-lactide), and poly(D,L-lactide-co-glycolide).

3. The method of claim 1, wherein the drug of the coating solution comprises at least one member of the group consisting of sirolimus, Biolimus, ridaforolimus, tacrolimus, temsirolimus, pimecrolimus, novolimus, myolimus, zotarolimus, everolimus, umirolimus, merilimus, 40-O-(3-hydroxypropyl)rapamycin, 40-O-[2-(2-hydroxy)ethoxy]-ethyl-rapamycin, 40-O-tetrazolylrapamycin, and 40-epi-(N1-tetrazolyl)-rapamycin.

4. The method of claim 1, wherein the albumin comprises human serum albumin, recombinant human serum albumin, sub-domains of human serum albumin cleaved from the other sub-domains, the recombinant equivalent to sub-domains of human serum albumin cleaved from the other sub-domains, or any combination thereof.

5. The method of claim 1, wherein the microparticulate albumin comprises particles consisting essentially of albumin.

6. The method of claim 1, wherein the microparticulate albumin comprises particles comprising albumin grafted onto a polymer.

7. The method of claim 6, wherein the polymer of the micro-particulate albumin comprises at least one member of the group consisting of poly(D,L-lactide), block copolymers of poly(D,L lactide) and polyethylene glycol, poly(D,L-lactide-co-glycolide), block copolymers of poly(glycolide) and polyethylene glycol, poly(L-lactide), block copolymers of poly(L-lactide) and polyethylene glycol, poly(caprolactone-co-L-lactide), poly(caprolactone-co-D,L-lactide), poly(caprolactone-co-glycolide), poly(caprolactone-block-L-lactide), poly(caprolactone-block-D,L-lactide), poly(caprolactone-block-glycolide), poly(ethylene-co-vinyl alcohol), polycysteine, polypropylene sulfide, polylysine, polyallylamine, polysaccharides, polyacrylates with pendant vinyl groups, poly(meth)acrylates with pendant vinyl groups, and poly-alpha-hydroxyesters.

8. The method of claim 1, wherein the solvent of the coating solution comprises acetone.

9. The method of claim 1, further comprising at least one additional processing operation.

10. The method of claim 1, wherein the medical device is a stent.

11. The method of claim 1, wherein the medical device is a bioabsorbable stent.

12. A method comprising:
disposing over a surface of a medical device a coating solution comprising microparticulate albumin, and an organic solvent; and
removing the solvent to form a coating comprising albumin;
wherein the microparticulate albumin comprises particles comprising albumin grafted onto a polymer.

13. The method of claim 12, wherein the polymer of the microparticulate albumin comprises at least one member of the group consisting of poly(D,L-lactide), block copolymers of poly(D,L lactide) and polyethylene glycol, poly(D,L-lactide-co-glycolide), block copolymers of poly(glycolide) and polyethylene glycol, poly(L-lactide), block copolymers of poly(L-lactide) and polyethylene glycol, poly(caprolactone-co-L-lactide), poly(caprolactone-co-D,L-lactide), poly(caprolactone-co-glycolide), poly(caprolactone-block-L-lactide), poly(caprolactone-block-D,L-lactide), poly(caprolactone-block-glycolide), poly(ethylene-co-vinyl alcohol), polycysteine, polypropylene sulfide, polylysine, polyallylamine, polysaccharides, polyacrylates with pendant vinyl groups, poly(meth)acrylates with pendant vinyl groups, and poly-alpha-hydroxyesters.

14. The method of claim 12, wherein the medical device is a stent.

15. The method of claim 14, wherein the medical device is a bioabsorbable stent.

16. The method of claim 12, further comprising at least one additional processing operation.

17. A method comprising:
disposing over a surface of a medical device a coating solution comprising microparticulate albumin, and acetone; and
removing the acetone to form a coating comprising albumin.

18. The method of claim 17, wherein the medical device is a stent.

19. The method of claim 18, wherein the medical device is a bioabsorbable stent.

20. The method of claim 17, further comprising at least one additional processing operation.

* * * * *